United States Patent [19]

Ito

[11] Patent Number: 4,505,891

[45] Date of Patent: Mar. 19, 1985

[54] MEDICINAL ADHESIVE SHEETS FOR HEART DISEASES AND A PROCESS FOR THE PREPARATION THEREOF

[75] Inventor: Toshio Ito, Tokyo, Japan

[73] Assignees: Nichiban Co., Ltd.; Nippon Kayaku Kabushiki Kaisha; Taiho Pharmaceutical Company, Limited, all of Tokyo, Japan

[21] Appl. No.: 387,885

[22] PCT Filed: Oct. 19, 1981

[86] PCT No.: PCT/JP81/00291

§ 371 Date: Jun. 9, 1982

§ 102(e) Date: Jun. 9, 1982

[87] PCT Pub. No.: WO82/01317

PCT Pub. Date: Apr. 29, 1982

[30] Foreign Application Priority Data

Oct. 20, 1980 [JP] Japan .............................. 55-146465

[51] Int. Cl.³ .................... A61K 9/70; A61L 15/03; A61F 13/00
[52] U.S. Cl. ................................................ 424/28
[58] Field of Search ........................................ 424/28

[56] References Cited

U.S. PATENT DOCUMENTS

| | | | |
|---|---|---|---|
| 4,420,470 | 12/1983 | Otsuka et al. ........................ | 424/28 |
| 4,421,737 | 12/1983 | Ito et al. .............................. | 424/28 |

FOREIGN PATENT DOCUMENTS

| | | | |
|---|---|---|---|
| 57-56424 | 4/1982 | Japan .................................. | 424/28 |
| 57-75917 | 5/1982 | Japan .................................. | 424/28 |
| 57-91913 | 6/1982 | Japan .................................. | 424/28 |
| 57-183714 | 11/1982 | Japan .................................. | 424/28 |
| 58-913 | 1/1983 | Japan .................................. | 424/28 |
| 2073588A | 10/1981 | United Kingdom ................ | 424/28 |
| 2093344A | 9/1982 | United Kingdom ................ | 424/28 |

*Primary Examiner*—Shep K. Rose
*Attorney, Agent, or Firm*—Oblon, Fisher, Spivak, McClelland & Maier

[57] ABSTRACT

A medicinal adhesive sheet for heart diseases having only slight irritation to the skin, which comprises an adhesive composition supported on a suitable base, the composition containing as essential ingredients a copolymer containing dodecyl methacrylate as main monomer component and a suitable amount of nitroglycerin, and the composition having an excellent nitroglycerin-releasing property and a good balance between adhesive strength and cohesive strength.

6 Claims, 7 Drawing Figures

MEDICINAL ADHESIVE SHEETS FOR HEART DISEASES AND A PROCESS FOR THE PREPARATION THEREOF

TECHNICAL FIELD

The present invention relates to medicinal adhesive sheets usable for the medical treatment and prevention of heart diseases. More particularly, the present invention relates to medicinal adhesive sheets containing nitroglycerin for heart diseases as the principal ingredient.

BACKGROUND ART

Nitroglycerin has long been used for the internal treatment of ischemic heart diseases. Nitroglycerin has been administered in the form of various preparations such as intravenous injection, sublingual tablets and ointments. The duration of the effects of intravenous injections, sublingual tablets and ointments are several minutes, 20–30 minutes and 3–5 hours, respectively.

Generally, sublingual tablets are used for the treatment of angina pectoris. However, their effects are short lived, and the sublingual tablets are therefore unsuitable for preventing an attach.

A nitroglycerin-containing ointment is used when the effects of nitroglycerin are to be maintained for a long period of time (for example, in preventing angina pectoris). When ointment is used, a suitable amount of the ointment is applied to the skin of the patient's chest and is then covered with a plastic film or the like and to prevent the volatilization of the nitroglycerin and staining of his clothes. The suitable amount of ointment is an amount slightly smaller than that which causes a headache. The ointment is applied in various amounts to the respective patients to determine the proper amount experimentally. At present, the amount of ointment is estimated from the length of the bead extruded from the tube, so determination of the precise quantity of the ointment is difficult. Further, the use of ointment is troublesome as described above.

(Prior Arts)

Recently, medicinal adhesive sheets containing nitroglycerin have been proposed (see the specification of Japanese Patent Laid-Open No. 2604/1980). However, the nitroglycerin retention and release of the sheets are unsatisfactory, since the adhesive contained therein has not been improved (an adhesive plaster base is used).

Copolymers of alkyl acrylates or alkyl methacrylates in which the alkyl group contains 4–12 carbon atoms have generally been used as adhesives only slightly irritating the skin. However, these conventional adhesives have a high ability to adsorb nitroglycerin and, therefore, a low nitroglycerin-releasing property. Thus, they are unsuitable for use as a carrier for nitroglycerin which is to be released as an active ingredient.

(Object of the Invention)

After investigations on adhesives having only a slight irritating effect on the skin and an excellent nitroglycerin-releasing property made under the above circumstances, the inventors have accomplished the present invention and the object has been attained.

DISCLOSURE OF THE INVENTION

(Construction of the Invention)

The object of the present invention has been attained by using a new copolymer developed by the inventors as an adhesive of an adhesive composition for medicinal adhesive sheets for heart diseases. The new copolymer is obtained by copolymerizing:

(a) about 60–98 parts by weight of dodecyl methacrylate, (b) about 2–40 parts by weight of a functional monomer, and (c) about 0–40 parts by weight of at least one short chain unsaturated monomer selected from the group consisting of vinyl acetate, alkyl acrylates in which the alkyl group contains 1–8 carbon atoms and alkyl methacrylates in which the alkyl group contains 1–8 carbon atoms.

In the present invention, the medicinal adhesive sheet for heart diseases is prepared by applying an adhesive composition containing the above copolymer and a suitable amount of nitroglycerin as the essential ingredient to a suitable base.

The description will be made on the constituents of the present invention.

(Copolymer)

(a) The suitable amount of dodecyl methacrylate constituting the copolymer according to the present invention is about 60–98 parts by weight as described above, and, more preferably, about 70–95 parts by weight.

(b) Suitable functional monomers according to the present invention include acrylic acid, methacrylic acid, acrylamide, methacrylamide, hydroxyethyl acrylate and hydroxyethyl methacrylate. Approximately 2–40 parts by weight, preferably about 2–10 parts by weight of the functional monomer is used. If the amount of the functional monomer is more than 40 parts by weight, the resulting copolymer has reduced adhesive power and a reduced nitroglycerin-releasing property. If the amount of the functional monomer is less than 2 parts by weight, the cohesive strength of the copolymer is insufficient and the copolymer becomes soft and sticky. Accordingly, in the latter case, the adhesive composition remains on the skin after the adhesive sheet has been peeled off.

(c) At least one short chain unsaturated monomer selected from the group consisting of vinyl acetate, alkyl acrylates in which the alkyl group contains 1–8 carbon atoms and alkyl methacrylates in which the alkyl group contains 1–8 carbon atoms can be used in an amount in the range of about 0–40 parts by weight, preferably up to about 30 parts by weight. The amount of these short chain unsaturated monomers should be determined in due consideration of the variety and amount of the above functional monomer (b), since they are used for controlling the cohesive strength of the copolymer depending on the variety and amount of monomer (b).

The copolymer used as the adhesive according to the present invention can be prepared by dissolving the monomers in a suitable solvent and heating the resulting solution to a suitable temperature under polymerization conditions. If a proper polymerization initiator is incorporated in the mixture in the polymerization vessel, the polymerization temperature can be lowered and the polymerization time required for obtaining a copolymer of a desired molecular weight can be reduced.

Ethyl acetate, n-hexane and toluene may be mentioned as organic solvents used for the preparation of the copolymer to be used as the adhesive.

A suitable reaction temperature for the preparation of the above copolymer is about 70° C.

A peroxide, particularly dodecyl peroxide, is a suitable polymerization initiator for preparation of the above copolymer. If a large amount of peroxide is used, it becomes difficult to control the polymerization procedure, though the polymerization reaction velocity is increased. On the other hand, if a small amount of peroxide is used, the polymerization reaction velocity is lowered and the molecular weight of the copolymer is apt to become too high. In case dodecyl peroxide is used, an amount of 12 parts by weight per 1,000 parts by weight of monomer mixture is suitable.

Peroxide is suitably used in the form of a solution with an organic solvent such as n-hexane. The peroxide solution is added to the mixture in the copolymerization reaction vessel when the temperature of the contents of the reaction vessel reaches the desired polymerization temperature (70° C). For safety, it is desirable to add the peroxide solution in small portions over, say, a period of one hour.

Under the above polymerization conditions, the polymerization time is preferably about 7-8 hours after the addition of the peroxide.

After completion of the polymerization reaction, a suitable organic solvent such as n-hexane is added to the reaction mixture in the vessel to dilute the copolymer solution, which is then removed from the vessel.

The copolymer content of the thus obtained copolymer solution is controlled to a concentration of 40 % to obtain an adhesive solution. The adhesive solution has a viscosity of about 160–550 poises at 30° C., as measured by a rotational viscometer. The viscosity of the thin film obtained by removing the solvent from the copolymer solution is about $9 \times 10^6$ poises to $7 \times 10^7$ poises as measured by the shearing creep method.

(Preparation of the adhesive composition)

In preparing the medicinal adhesive sheets of the present invention, nitroglycerin is incorporated in the above copolymer solution in an amount to yield a content of 1-20 mg, preferably 5-15 mg, per 100 cm² of sheet.

Nitroglycerin is incorporated in the above copolymer solution by mixing the copolymer solution diluted with the organic solvent with a solution of nitroglycerin in an organic solvent in a ordinary manner.

The organic solvent in which the nitroglycerin is dissolved should not coagulate the copolymer when it is mixed with the copolymer solution. In regard to this point, ethyl acetate is suitable as the organic solvent for nitroglycerin. The nitroglycerin concentration in the solution with the organic solvent should be low enough to avoid danger of explosion. A suitable concentration thereof is in the range of about 3 to 7 wt. %.

A suitable softener may be incorporated in the adhesive composition of the medicinal adhesive sheets of the present invention so as to improve the adhesion of the composition and to control the retention and release of nitroglycerin. Suitable softeners are long chain fatty acid esters such as isopropyl myristate and isopropyl lanolin fatty acid esters; lanolin derivatives such as refined lanolin, hydrogenated lanolin, lanolin alcohols and lanolin acetate; fatty acid monoglycerides such as glycerin monostearate; oils and fats such as hydrogenated castor oil; low softening point resins such as methyl ester of hydrogenated rosin; and vaseline. These softeners are used in an amount of about 5 to 40 parts by weight per 100 parts by weight of adhesive.

(Base)

Materials used as the base of the medicinal adhesive sheets of the present invention are those generally used as the base of adhesive tapes but they should neither be permeable to nitroglycerin nor inhibit the release of nitroglycerin. Among them, polyolefins such as polyethylene and polypropylene are most suitable from the viewpoint of stability on standing.

(Method of applying the adhesive composition to the base)

The medicinal adhesive sheets of the present invention comprise the above adhesive composition adhered to a base. The adhesive composition may be applied to the base by the coating method or the transfer method generally employed for the preparation of adhesive tapes.

The medicinal adhesive sheets of the present invention may be prepared also by a new precise transfer method. This new method will be illustrated below.

Step 1

A silicone resin is applied to a polyethylene layer of a release paper comprising a laminate of paper and a polyethylene layer. A solution of dodecyl methacrylate copolymer of the present invention is applied to the silicone-treated surface and then dried.

Step 2

One surface of a plastic film (i.e. the base) such as flexible polyethylene film is corona-treated and the other surface is mat-finished. The corona-treated surface of the thus obtained base and the copolymer surface of the composite (release paper carrying the copolymer) obtained in above step 1 are attached together to obtain a sheet in which the copolymer is interposed between the release paper and the base.

Step 3

Silicone resin is applied to the surface of a plastic film having high dimensional stability, such as a polyethylene terephthalate film, to form a separator. A nitroglycerin-containing ointment is applied to the silicone-treated surface. The nitroglycerin-containing ointment comprises a softener such as refined lanolin in which nitroglycerin is homogeneously dispersed.

Step 4

The release paper is removed from the copolymer sheet having the release paper and the base obtained in above step 2 to expose the copolymer. The copolymer surface and the ointment surface on the separator obtained in above step 3 are adhered together. The thus obtained composite is heated to a temperature of 25°–60° C., preferably 40°–50° C. (at which nitroglycerin is neither volatilized nor decomposed), and the composite is kept at that temperature for several days (for example, 6–8 days) to age it. By this treatment, the nitroglycerin-containing ointment is diffused in the copolymer to form a homogeneous nitroglycerin-containing adhesive composition on the base, and the medicinal adhesive sheet having the separator of the present invention is thus obtained.

According to the new transfer method above, the sheet of the present invention can be prepared with constant, stable precision.

However, when the sheet does not need to be of high precision, a simplified transfer method may be employed in place of the above new transfer method. The simplified transfer method consists of the following:

Step 1

One surface of a plastic film (i.e. the base) such as polypropylene film is corona-treated and the other surface thereof is mat-finished. The dodecyl methacrylate copolymer of the present invention is applied to the corona-treated surface of the base to obtain a copolymer sheet carried on the base.

Step 2

The same treatment as in step 3 of the precise transfer method is carried out.

Step 3

The copolymer surface of the copolymer sheet obtained in step 1 and the ointment surface on the separator obtained in above step 2 are adhered together. Thus resulting composite is heated and aged in the same manner as in the second half of step 4 of the above precise transfer method to obtain the medicinal adhesive sheet of the present invention.

(Shape of the Medicinal Adhesive Sheet)

The medicinal adhesive sheet of the present invention may be in the form of a roll like an adhesive tape or, more preferably, in the form of suitably sized sheets. If it is in the form of sheets, it is easy for the patients to control the dosage. If each sheet is sealed in an aluminum bag, the volatilization of nitroglycerin can be prevented until use.

When the sheets are prepared, a separator should be adhered to the adhesive composition. As materials for the separator, those which prevent migration of nitroglycerin on standing, such as polyesters, polyethylene, polypropylene and aluminum-laminated polyolefins, may be used. The surface of the separator in contact with the adhesive composition is preferably treated with a silicone resin to facilitate its release from the adhesive composition.

(Functions and effects of the present invention)

High molecular substances having dodecyl methacrylate as the main monomer have hardly been used as a component of an adhesive composition in the prior art. The medicinal adhesive sheet of the present invention is characterized by such a copolymer as the main component of the adhesive composition.

The medicinal adhesive sheet of the present invention has a good balance between adhesiveness and cohesive strength of the adhesive composition, and exhibits only slight irritation to the skin.

Known acrylic adhesives (for example polymers such as poly-2-ethylhexyl acrylate) generally have an offensive smell, but the dodecyl methacrylate copolymers contained in the medicinal adhesive sheet of the present invention have no unpleasant smell and, therefore, the sheet of this invention is more comfortable to use.

As compared with a medicinal adhesive sheet containing an adhesive composition containing an alkyl acrylate or alkyl methacrylate in which the alkyl group contains 4–8 carbon atoms as the main component, the medicinal adhesive sheet of the present invention has a superior nitroglycerin-releasing property. Examples from tests are given below.

(Sample A)

An adhesive sheet was prepared from an ordinary acrylic copolymer composition comprising 85 wt. % of 2-ethylhexyl acrylate as the main constituent and 10 wt. % of vinyl acetate and 5 wt. % of acrylic acid as sub-constituents (viscosity of a 40 wt. % solution in a mixture of toluene and cyclohexane at 30° C. was 60 poises) and containing 2%, based on the solid content of the acrylic copolymer, of nitroglycerin. The adhesive sheet had a polyethylene base and an adhesive layer thickness of 40 microns. The nitroglycerin elution rate from the adhesive sheet into a phosphate buffer physiological salt solution (pH 6.0) was about 18% at 37° C. after 60 minutes. Sections (5×7 cm$^2$) (actual nitroglycerin content: 2.8 mg) of the sheet were applied to normal human subjects but no reaction was recognized.

(Sample B)

The elution rate of an adhesive sheet prepared from a solution of dodecyl methacrylate copolymer (comprising 86 wt. % of dodecyl methacrylate as main ingredient and 10 wt. % of vinyl acetate and 4 wt. % of acrylic acid as sub-constituents) obtained according to "Preparation Example 1 for adhesive copolymer solution" given below and containing 2%, based on the solid content of the copolymer, of nitroglycerin was improved to about 46% under the same conditions as in the test of Sample A. Sections (5×7 cm$^2$) (actual nitroglycerin content: 3.0 mg) of the sheet were applied to normal human subjects. Approximately two hours after application a slight headache and elevation of heart rate were recognized. About 40 minutes after removal of the test pieces the subjective symptoms disappeared.

BRIEF DESCRIPTION OF THE DRAWINGS

In FIG. 2, (a) shows a release paper with copolymer applied, (b) shows the copolymer affixed to a base, (c) shows the copolymer from which the release paper has been peeled, (d) shows a nitroglycerin-containing softener applied to a separator, (e) shows (c) affixed to (d), and (f) shows the condition after aging (e). In FIG. 2, 1 represents a release paper, 2 represents a copolymer, 3 represents a base, 4 represents a separator, 5 represents a nitroglycerin-containing ointment and 6 represents a nitroglycerin-containing adhesive composition.

BEST MODE FOR CARRYING OUT THE INVENTION

Figure 1:
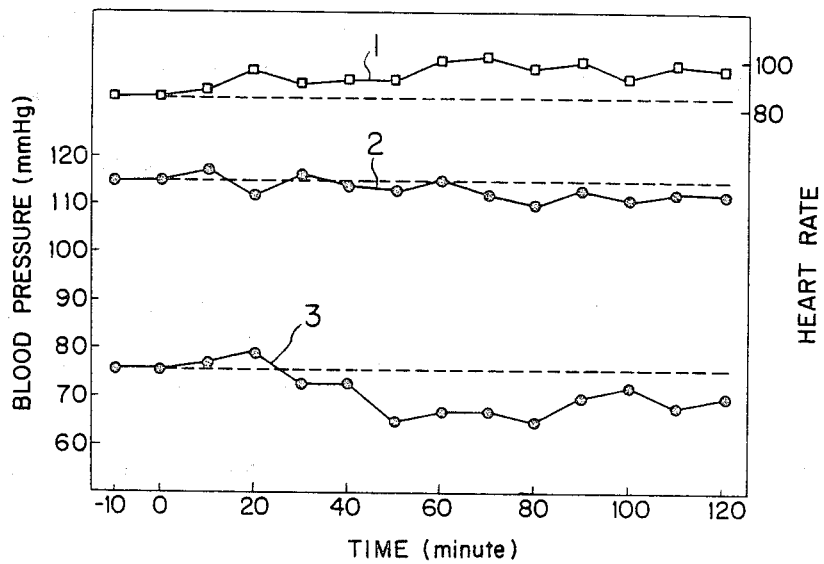
FIG. 1 is a line graph showing the test results of the medicinal adhesive sheet of the present invention. Line 1 indicates heart rate, line 2 indicates systolic blood pressure and line 3 indicates diastolic blood pressure.
Figure 2A:
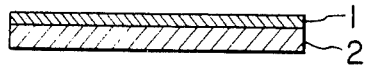
FIG. 2 illustrates the respective steps in the preparation method shown in Example 2.
Figure 2B:
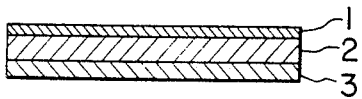
Figure 2C:
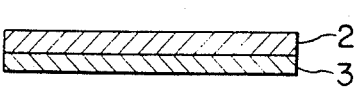
Figure 2D:
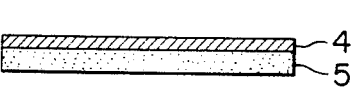
Figure 2E:
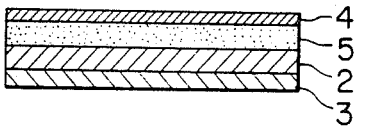
Figure 2F:
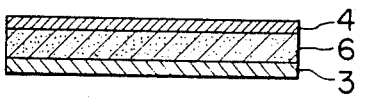

Before the description of embodiments of the medicinal adhesive sheets of the present invention, a description of the methods of preparing copolymer adhesive solutions used for the preparation of the adhesive compositions will be given.

PREPARATION EXAMPLE 1 OF THE ADHESIVE COPOLYMER SOLUTION 860 g of dodecyl methacrylate, 100 g of vinyl acetate, 40 g of acrylic acid, 560 g of n-hexane and 120 g of toluene is charged in a 4 l four-necked flask provided with a nitrogen inlet, reflux condenser, stirrer and thermometer. The whole is heated in a water bath and stirred while nitrogen is introduced therein. When the inner temperature reaches 70° C., a solution of 12 g of dodecyl peroxide as initiator dissolved in 88 g of n-hexane is slowly added over a period of one hour. The reaction is continued for 7 hours. After completion of the polymerization reaction, 720 g of n-hexane is added to the mixture to dilute the same, thereby obtaining 2500 g of an adhesive solution having a concentration of about 40%. The solution has a viscosity of 166 poises, determined with a rotational viscometer at 30° C. After the removal of the solvent, the resulting thin film of the adhesive solution has a viscosity of $6.05 \times 10^7$ poises as determined by shearing creep method.

PREPARATION EXAMPLE 2 OF THE ADHESIVE COPOLYMER SOLUTION 760 g of dodecyl methacrylate, 200 g of 2-ethylhexyl acrylate, 40 g of acrylic acid, 560 g of n-hexane and 120 g of toluene are charged in a 4 l four-necked flask provided with a nitrogen inlet, reflux condenser, stirrer and thermometer. The whole is heated in a water bath and stirred while nitrogen is introduced therein. When the inner temperature reaches 70° C., a solution of 12 g of dodecyl peroxide as initiator in 88 g of n-hexane is slowly added over a period of about one hour. The stirring is continued for an additional 7 hours. After the completion of the polymerization reaction, 720 g of n-hexane is added to the mixture to dilute the same, thereby obtaining 2500 g of an adhesive solution having a concentration of about 40%. The adhesive solution has a viscosity of 530 poises at 30° C. as determined by means of a rotational viscometer. After removal of the solvent, the resulting thin film of the adhesive solution has a viscosity of $9.50 \times 10^6$ poises as determined by the shearing creep method.

PREPARATION EXAMPLE 3 FOR THE ADHESIVE COPOLYMER SOLUTION 950 g of dodecyl methacrylate, 50 g of acrylic acid, 560 g of n-hexane and 120 g of toluene are charged in a 4 l four-necked flask provided with a nitrogen inlet, reflux condenser, stirrer and thermometer. The whole is heated in a water bath and stirred while nitrogen is introduced therein. When the inner temperature reached 70° C., a solution of 12 g of dodecyl peroxide as initiator in 88 g of n-hexane is slowly added over a period of about one hour. The stirring is continued for an additional 7 hours. After completion of the polymerization reaction, 720 g of n-hexane is added to the mixture to dilute it, thereby obtaining 2500 g of an adhesive solution having a concentration of about 40%. The adhesive solution has a viscosity of 378 poises as determined by means of a rotational viscometer at 30° C. After removal of the solvent, the resulting thin film of the adhesive has a viscosity of $3.41 \times 10^7$ poises as determined by the shearing creep method.

The following examples will further illustrate, but by no means limit, the present invention.

EXAMPLE 1

160 g (i.e. 40% based on the solid content of adhesive solution) of 5% solution of nitroglycerin in ethyl acetate was added to 1000 g of the adhesive copolymer solution obtained in the above Preparation Example 1 and the whole was thoroughly stirred to obtain a mixture. The resulting nitroglycerin-containing adhesive composition was uniformly applied to the surface of a silicone-treated polypropylene film separator 80 μm thick so that the solid content of the adhesive composition would be 40 g/m². The solvent was volatilized out to obtain a nitroglycerin-containing adhesive composition in the form of a sheet.

Separately, one surface of a flexible polyethylene film 80 μm thick was mat-finished and the other surface was corona-treated to obtain a base.

The adhesive composition layer of the adhesive composition sheet provided with the separator and the corona-treated surface of the base were adhered together, thereby transferring the adhesive composition from the separator to the polyethylene film base. Thus, a medicinal adhesive sheet containing 8 mg/100 cm² of nitroglycerin was obtained. The sheet was cut into pieces of a given size and each piece was sealed in an aluminum-laminated polyethylene bag.

Results of elution test of the medicinal adhesive sheet wherein a phosphate buffer physiological salt solution (pH 6.0) was used are summarized in following Table 1.

EXAMPLE 2

An example of the precise transfer method of the present invention will be illustrated with reference to FIG. 2, which faciliates understanding this example.

Adhesive solution (2) obtained from the above Preparation Example 2 was uniformly applied to a release paper (1) laminated with a silicone-treated polyethylene layer in such a manner that the solid content would be 32 g/m², and then it was dried [see FIG. 2-(a)]. Adhesive (2) on the release paper was affixed to the corona-treated surface of base (3) comprising a flexible polyethylene film 8 μm thick with one mat-finished surface and one corona-treated surface to obtain a polyethylene sheet in which the copolymer was interposed between the release paper and the base [FIG. 2-(b)].

Then, ointment (5) comprising refined lanolin with 10% of uniformly dispersed nitroglycerin was applied in an amount of 8 g/m² to the silicone surface of a silicone-treated polyethylene terephthalate film separator (4) having a thickness of 80 μm [FIG. 2-(d)]. The said surface is attached to the adhesive surface (2) [FIG. 2-(c)] exposed by removing the release paper from the polyethylene sheet [FIG. 2-(e)]. After aging at 40° C. for approximately 7 days, a nitroglycerin-containing adhesive sheet (nitroglycerin content: 8 mg/100 cm²) having a polyethylene base and a polyethylene terephthalate separator [FIG. 2-(f)] was obtained. The sheet was cut into pieces of a given size and each piece was sealed in an aluminum-laminated polyethylene bag. The bags were stored. Results of an elution test of the medicinal adhesive sheet using a phosphate buffer physiological salt solution (pH 6.0) are summarized in Table 1. The steps of this example are shown in FIG. 2.

EXAMPLE 3

20 g of white petrolatum and 140 g of refined lanolin was added to 1000 g of the adhesive solution obtained in Preparation Example 3, and the whole was thoroughly stirred to obtain a solution. Then 224 g (i.e. 40% based on the solid copolymer content) of 5% solution of nitroglycerin in ethyl acetate was added to the adhesive composition to obtain a mixture. The nitroglycerin-containing adhesive solution was uniformly applied to a silicone-treated polypropylene film separator having a thickness of 80 μm so that the solid content would be 40 g/m². The solvent was volatilized to obtain an adhesive composition sheet.

Separately, one surface of a flexible polyethylene film 80 μm thick was mat-finished and the other surface was corona-treated to obtain a base.

The adhesive surface of the adhesive composition sheet was attached to the corona-treated surface of the base to obtain a medicinal adhesive sheet containing 8 mg/100 cm² of nitroglycerin. The sheet was cut into pieces of a given size and each piece was sealed in an aluminum-laminated polyethylene bag. The bags were stored. Results of elution test of the medicinal adhesive sheet using a phosphate buffer physiological salt solution (pH 6.0) are summarized in Table 1.

EXAMPLE 4

160 g (i.e. 40% based on the solid content of the adhesive solution) of 5% solution of nitroglycerin in ethyl acetate was added to 1000 g of the adhesive solution obtained in Preparation Example 2 and the mixture was stirred thoroughly. The nitroglycerin-containing adhesive solution was uniformly applied to a silicone-treated polyethylene terephthalate film separator having a thickness of 80 μm so that the solid copolymer content would be 40 g/m². The solvent was volatilized to obtain an adhesive composition sheet.

Separately, one surface of a flexible polyethylene film 80 μm thick was mat-finished and the other surface was corona-treated to obtain a base.

The adhesive layer surface of the adhesive composition sheet was attached to the corona-treated surface of the base to obtain a nitroglycerin-containing medicinal adhesive sheet having a nitroglycerin content of 8 mg/100 cm². The sheet was cut into pieces of a given size and each piece was sealed in an aluminum-laminated polyethylene bag. The bags were stored. Results of elution test of the medicinal adhesive sheet using a phosphate buffer physiological salt solution (pH 6.0) are summarized in Table 1 given below.

REFERENTIAL EXAMPLE 1: ELUTION TEST OF NITROGLYCERIN-CONTAINING MEDICINAL ADHESIVE SHEET

Nitroglycerin elution test of a nitroglycerin-containing medicinal adhesive sheet was carried out using a phosphate buffer physiological salt solution (0.05 mol, pH 6.0). The nitroglycerin-containing adhesive sheet was cut into round pieces having a radius of 2 cm and applied to a cellulose film, then mounted on a fixing table on an acrylic disc. It was immersed in 50 ml of the phosphate buffer physiological salt solution at 37° C. and the solution was slowly stirred at a given rate. Amounts of nitroglycerin eluted out through the cellulose film after one, two and four hours were measured by means of a microbonder pack $C_{18}$ (a product of Waters) column by high performance liquid chromatography.

The results of the analysis of the samples in Examples 1 to 4 are summarized in Table 1. All of the samples of the present invention exhibited a higher nitroglycerin elution than that of a sample prepared by using a commercially available acrylic adhesive.

TABLE 1

Results of elution tests of nitroglycerin-containing adhesive sheets

| Sample | Elution time (hr.) | | |
|---|---|---|---|
| | 1 | 2 | 4 |
| Medicinal adhesive sheet of Example 1 | 46.5 | 60.1 | 78.8 |
| Medicinal adhesive sheet of Example 2 | 55.7 | 72.6 | 89.7 |
| Medicinal adhesive sheet of Example 3 | 49.2 | 62.4 | 80.2 |
| Medicinal adhesive sheet of Example 4 | 53.4 | 74.7 | 92.4 |
| Tape containing commercially available acrylic adhesive* | 18.0 | 26.7 | 35.0 |

Numerals in Table 1 are elution rates (%) into the phosphate buffer physiological salt solution (pH 6.0). The initial nitroglycerin content of the sheet is shown as 100%.
*Tape pieces were prepared in the same manner as in Example 1 except that a commercially available acrylic adhesive (the same copolymer as in above sample A was used.

REFERENCE EXAMPLE 2: NITROGLYCERIN RESIDUE IN THE NITROGLYCERIN-CONTAINING ADHESIVE SHEET AFTER THE APPLICATION THEREOF

A nitroglycerin-containing adhesive tape was applied to the inner side of the forearm of each of three normal male human subjects. After a given period of time, the adhesive tape was peeled off and the amount of nitroglycerin remaining in the tape was measured by HPLC. The results are summarized in Table 2.

TABLE 2

| Sample | Application time (hr.) | | | |
|---|---|---|---|---|
| | 1 | 2 | 4 | 8 |
| Medicinal adhesive tape of Example 1 | 96.2 | 94.3 | 82.9 | 64.8 |
| Medicinal adhesive tape of Example 2 | 91.6 | 84.2 | 78.4 | 62.7 |
| Medicinal adhesive tape of Example 3 | 98.5 | 92.6 | 80.4 | 65.2 |
| Medicinal adhesive tape of Example 4 | 84.9 | 81.3 | 73.7 | 59.0 |
| Tape containing commercially available acylic adhesive* | 100.1 | 94.1 | 90.7 | 79.4 |

*Same sample as in Table 1.

Numerals in Table 2 are nitroglycerin residues (%) in the nitroglycerin-containing adhesive tapes after they were applied to an inner side of the forearms of three normal male human subjects. The initial value is represented as 100%.

In all of the medicinal adhesive tapes according to the present invention containing dodecyl methacrylate as the main ingredient, the nitroglycerin residue after application was smaller than that of the commercially available acrylic adhesive-containing tape. The balance obtained by deducting the residue (%) from the initial value (100%) indicates the percutaneous absorption. Accordingly, the nitroglycerin-containing adhesive sheet of the present invention shows high percutaneous absorption.

REFERENCE EXAMPLE 3: CHANGES IN BLOOD PRESSURE AND HEART RATE DUE TO THE NITROGLYCERIN-CONTAINING ADHESIVE SHEET

The nitroglycerin-containing adhesive sheet of Example 4 was applied to a normal male human subject (age: 38) and his blood pressure, heart rate and electrocardiogram (lead II) were recorded. He was kept resting lying on his back from 30 minutes before the application. The said sheet ($5 \times 10$ cm$^2$) (actual nitroglycerin content: 4.1 mg) was applied to the inner side of one forearm of the subject. Blood pressure and electrocardiogram were measured at 10 minute intervals and the heart rate was measured continuously. The test was continued for two hours. The results are summarized in FIG. 1.

The blood pressure reduction or heart rate increase and palpitation began about 20 minutes after the application of the sample sheet. The subject complained of a weak headache 60 minutes after application. The palpitation of the subject became severe 90 minutes after application. The blood pressure reduction and heart rate increase substantially coincided with the appearance of the subjective symptoms of the patient, but influences on the electrocardiogram were hardly observed. It is apparent, therefore, that the medicinal adhesive sheet of the present invention is suitable for the treatment of heart diseases and prevention of an attack if the area of the sheet (amount of the medicine) is suitably determined.

INDUSTRIAL UTILITY

The medicinal adhesive sheet of the present invention has an excellent nitroglycerin-releasing property and can be easily used. The sheet, therefore, can be used for the treatment and prevention of ischemic heart diseases such as angina pectoris. It is expected, therefore, that the present invention will contribute to the development of the pharmaceutical industry.

What is claimed is:

1. A medicinal adhesive sheet for heart diseases comprising an adhesive composition comprising:
   (A) a copolymer obtained by copolymerizing (a) about 60–98 parts by weight of dodecyl methacrylate, (b) about 40–2 parts by weight of a functional monomer and (c) about 0–40 parts by weight of at least one short chain unsaturated monomer selected from the group consisting of vinyl acetate, alkyl acrylates in which the alkyl group contains 1–8 carbon atoms and alkyl methacrylates in which the alkyl group contains 1–8 carbon atoms, and
   (B) nitroglycerin;
   wherein said adhesive composition is supported on a base and is covered with a separator.

2. The medicinal adhesive sheet for heart diseases according to claim 1, wherein said separator is a film selected from the group consisting of films of polyesters, polyethylene, polypropylene, and aluminum foil-laminated polyolefins.

3. The medicinal adhesive sheet for heart diseases according to claim 1, wherein said functional monomer is selected from the group consisting of acrylic acid, methacrylic acid, acrylamide, methacrylamide, hydroxyethyl acrylate and hydroxyethyl methacrylate.

4. The medicinal adhesive sheet for heart diseases according to claim 1, wherein said nitroglycerin is present in the amount of 1 to 20 mg per 100 cm$^2$ of sheet.

5. The medicinal adhesive sheet for heart diseases according to claim 1, wherein said adhesive composition further comprises a softener selected from the group of isopropyl myristate, isopropyl lanolin fatty acid ester, refined lanolin, hydrogenated lanolin, lanolin alcohols, lanolin acetate, glycerin monostearate, hydrogenated castor oil, methyl ester of hydrogenated rosin and vaseline.

6. The medicinal adhesive sheet for heart diseases according to claim 5, wherein said softener is present in the amount of about 5 to 40 parts by weight per 100 parts by weight of adhesive.

* * * * *